(12) United States Patent
Mitelberg et al.

(10) Patent No.: US 8,574,260 B2
(45) Date of Patent: *Nov. 5, 2013

(54) EMBOLIC DEVICE DELIVERY SYSTEM WITH RETRACTABLE PARTIALLY COILED-FIBER RELEASE

(75) Inventors: Vladimir Mitelberg, Aventura, FL (US); William W. Sowers, Pembroke Pines, FL (US)

(73) Assignee: DePuy Synthes Products, LLC, Raynham, MA (US)

( * ) Notice: Subject to any disclaimer, the term of this patent is extended or adjusted under 35 U.S.C. 154(b) by 188 days.

This patent is subject to a terminal disclaimer.

(21) Appl. No.: 12/944,423

(22) Filed: Nov. 11, 2010

(65) Prior Publication Data

US 2011/0060360 A1    Mar. 10, 2011

Related U.S. Application Data

(63) Continuation of application No. 11/189,581, filed on Jul. 26, 2005, now Pat. No. 7,918,872.

(60) Provisional application No. 60/592,724, filed on Jul. 30, 2004.

(51) Int. Cl.
*A61M 29/00* (2006.01)

(52) U.S. Cl.
USPC .......................................................... 606/200

(58) Field of Classification Search
USPC ......................................... 606/139, 142, 200
See application file for complete search history.

(56) References Cited

U.S. PATENT DOCUMENTS

| 5,108,407 A | 4/1992 | Geremia |
| 5,122,136 A | 6/1992 | Guglielmi |
| 5,263,964 A | 11/1993 | Purdy |
| 5,304,195 A | 4/1994 | Twyford, Jr. |
| 5,334,210 A | 8/1994 | Gianturco |
| 5,350,397 A | 9/1994 | Palermo |
| 5,382,259 A | 1/1995 | Phelps |
| 5,527,338 A | 6/1996 | Purdy |
| 5,540,660 A | 7/1996 | Jenson |
| 5,540,680 A | 7/1996 | Guglielmi |

(Continued)

FOREIGN PATENT DOCUMENTS

| EP | 1159922 A2 | 12/2001 |
| EP | 1188413 A2 | 3/2002 |
| WO | WO 0072781 A2 | 12/2000 |

OTHER PUBLICATIONS

U.S. Appl. No. 11/189,581, Non-Final Rejection dated May 23, 2008.

(Continued)

*Primary Examiner* — Corrine M McDermott
*Assistant Examiner* — Alexander Orkin

(57) ABSTRACT

A medical device for placing an embolic device, such as an embolic coil, at a predetermined site within a vessel of the body including a delivery catheter and a flexible pusher member slidably disposed within the lumen of the catheter. An embolic device having a headpiece coupled to the proximal end is releasably disposed within the distal end of the pusher member and retained in place by a retractable fiber, having a coiled distal portion. When the embolic device is advanced to the predetermined site within the vessel, the detachment fiber is retracted from around the headpiece of the embolic device to thereby release the embolic device.

10 Claims, 2 Drawing Sheets

(56) References Cited

U.S. PATENT DOCUMENTS

| | | | |
|---|---|---|---|
| 5,578,074 | A | 11/1996 | Mirigian |
| 5,690,667 | A | 11/1997 | Gia |
| 5,772,668 | A | 6/1998 | Summers |
| 5,891,130 | A | 4/1999 | Palermo |
| 5,895,385 | A | 4/1999 | Guglielmi |
| 5,895,391 | A * | 4/1999 | Farnholtz ............... 606/108 |
| 5,895,411 | A | 4/1999 | Irie |
| 5,925,037 | A | 7/1999 | Guglielmi |
| 5,925,059 | A | 7/1999 | Palermo |
| 5,964,771 | A | 10/1999 | Beyar |
| 5,976,126 | A | 11/1999 | Guglielmi |
| 6,093,199 | A | 7/2000 | Brown |
| 6,165,198 | A | 12/2000 | McGurk |
| 6,203,547 | B1 | 3/2001 | Nguyen |
| 6,299,619 | B1 | 10/2001 | Greene, Jr. |
| 6,428,557 | B1 | 8/2002 | Hilaire |
| 6,468,266 | B1 | 10/2002 | Bashiri |
| 6,468,288 | B1 | 10/2002 | Manning |
| 6,478,773 | B1 | 11/2002 | Gandhi |
| 6,494,884 | B2 | 12/2002 | Gifford, III |
| 6,530,934 | B1 | 3/2003 | Jacobsen |
| 6,835,185 | B2 | 12/2004 | Ramzipoor |
| 2002/0165569 | A1 | 11/2002 | Ramzipoor |
| 2003/0208256 | A1 | 11/2003 | DiMatteo |
| 2004/0034363 | A1 | 2/2004 | Wilson |
| 2004/0098024 | A1 | 5/2004 | Dieck |
| 2004/0153120 | A1 | 8/2004 | Seifert |
| 2005/0043755 | A1 | 2/2005 | Wilson |
| 2005/0222605 | A1 * | 10/2005 | Greenhalgh et al. ......... 606/200 |
| 2006/0025801 | A1 | 2/2006 | Lulo |

OTHER PUBLICATIONS

U.S. Appl. No. 11/189,581, Non-Final Rejection dated Oct. 8, 2008.
U.S. Appl. No. 11/189,581, Final Rejection dated Dec. 22, 2009.
U.S. Appl. No. 11/189,581, Non-Final Rejection dated Jun. 1, 2010.

* cited by examiner

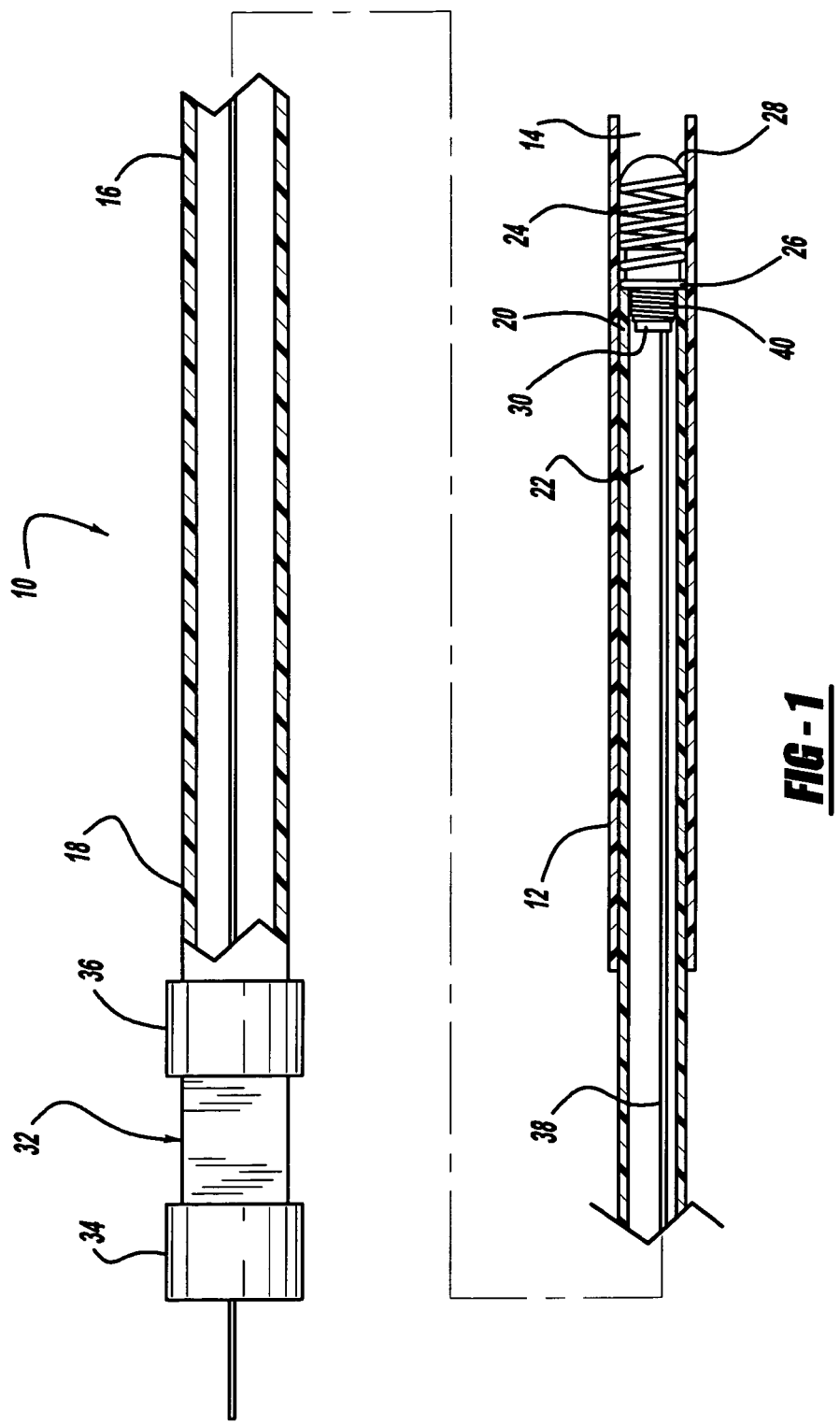

EMBOLIC DEVICE DELIVERY SYSTEM WITH RETRACTABLE PARTIALLY COILED-FIBER RELEASE

CROSS-REFERENCE TO RELATED APPLICATIONS(S)

The present application is a continuation of U.S. patent application Ser. No. 11/189,581 filed Jul. 26, 2005 (now granted U.S. Pat. No. 7,918,872, issued Apr. 6, 2011), which claims priority from Provisional Patent Application Ser. No. 60/592,724, filed on Jul. 30, 2004.

BACKGROUND OF INVENTION

1. Field of the Invention

The present invention relates to a medical device for placing an embolic device, such as an embolic coil, at a predetermined site within a vessel, and more particularly relates to a catheter based deployment system for delivering an embolic coil. This device is particularly suited to transport an embolic device, through the tortious vasculature of the human brain and to the predetermined site within the vessel.

2. Description of the Prior Art

For many years, flexible catheters have been used to place various devices within the vasculature of the human body. Such devices include dilation balloons, radiopaque fluids, liquid medications, and various types of occlusion devices such as balloons and embolic coils. Examples of such catheter-based devices are disclosed in U.S. Pat. No. 5,108,407, entitled "Method and Apparatus for Placement of an Embolic Coil;" and U.S. Pat. No. 5,122,136, entitled "Endovascular Electrolytically Detachable Guidewire Tip for the Electroformation of Thrombus in Arteries, Veins, Aneurysms, Vascular Malformations and Arteriovenous Fistulas." These patents disclose catheter-based devices designed to deliver embolic coils to a predetermined site within a vessel of the human body in order to treat aneurysms, or alternatively, to occlude a blood vessel at a particular location.

Coils which are placed in vessels may take the form of helically wound coils, or alternatively, may take the form of randomly wound coils, coils wound within coils or other such coil configurations. Examples of various coil configurations are disclosed in U.S. Pat. No. 5,334,210, entitled "Vascular Occlusion Assembly;" and U.S. Pat. No. 5,382,259, entitled, "Vasoocclusion Coil with Attached Tubular Woven or Braided Fibrous Covering." Embolic coils are generally formed of a radiopaque metallic material, such as platinum, gold, tungsten, or an alloy of these metals. Often, several coils are placed at a given location to occlude the flow of blood through the vessel or aneurysm by promoting thrombus formation at the particular location.

Additionally, embolic coils have been placed within the distal end of a catheter, such that when the distal end of the catheter is properly positioned, the coil may then be pushed out of the end of the catheter with a pusher member to release the coil at the predetermined site within the vessel. This procedure for placement of the embolic coil is conducted under fluoroscopic visualization, such that the movement of a coil through the vasculature of the body may be monitored, and the coil may be placed in the desired location.

Another procedure involves the use of glue or solder to attach the coil to a guidewire, which is then placed within a flexible catheter for positioning the coil at a predetermined site within the vessel. Once the coil is at the predetermined site, the catheter holds the coil in position, and the guidewire is pulled proximally of the catheter to thereby detach the coil from the guidewire. Such a coil positioning system is disclosed in U.S. Pat. No. 5,263,964 entitled, "Coaxial Traction Detachment Apparatus and Method."

Still another coil positioning procedure is that of having a catheter with a socket at the distal end, such that it retains a ball that is bonded to the proximal end of the coil. The ball, generally larger in diameter than the outside diameter of the coil, is placed in a socket within the lumen at the distal end of the catheter, and the catheter is then moved into a vessel in order to place the coil at a predetermined location. Once the site is reached, a pusher wire with a piston at the end thereof is pushed distally from the proximal end of the catheter to push the ball out of the socket, in order to release the coil at the predetermined site. Such a system is disclosed in U.S. Pat. No. 5,350,397, entitled, "Axially Detachable Embolic Coil Assembly."

Another procedure for placing an embolic coil at a predetermined site within a vessel is that of using a heat releasable adhesive bond for retaining the coil at the distal end of the catheter. One such system uses laser energy transmitted through a fiber optic cable to apply heat to the adhesive bond in order to release the coil from the distal end of the catheter. Such a procedure is disclosed in aforementioned U.S. Pat. No. 5,108,407.

Still another coil deployment system incorporates an interlocking mechanism with the coil. The interlocking end of the embolic coil couples with a similar interlocking end on a pusher assembly. A control wire extends through the two interlocking ends to secure the coil to the pusher assembly. The pusher assembly and embolic coil are initially disposed within the lumen of a catheter. When the embolic coil is pushed out of the end of the catheter for placement, the control wire is retracted and the coil disengages from the pusher assembly. Such a deployment system is disclosed in U.S. Pat. No. 5,925,059, entitled, "Detachable Embolic Coil Assembly."

Yet another coil deployment system incorporates an embolic device detachably mounted on the distal portion of a pusher member and held in place with a connector thread or fiber. The fiber passes through a cutter member that may be activated to cut the connector fiber. Once the connector fiber is cut, the embolic device is released. Such a deployment system is disclosed in Published U.S. Patent Application No. 2002/0165569, and entitled, "Intravascular Device Deployment Mechanism Incorporating Mechanical Detachment."

Still another coil deployment system incorporates an embolic device with a stretch resistant member therethrough. The distal end of the stretch resistant member is attached to the embolic coil, and the proximal end of the stretch resistant member is detachably mounted on an elongated pusher member to allow for placement and release of the coil within a vessel. The stretch resistant member is detachably mounted on the pusher member through various means, such as adhesive or by a connector fiber adhered to or tied onto the pusher member and is detachable by the application of heat. Such a deployment system is disclosed in Published U.S. Patent Application No. 2004/0034363, entitled, "Stretch Resistant Therapeutic Device."

Still another coil deployment system incorporates a platinum wire and or tip that is inserted into a vascular cavity. The tip may be elongated and flexible, folded upon itself several times, or may have a branched configuration. The tip may be separated from the wire mechanically or via electrolytic separation. Such a system is disclosed in U.S. Pat. Nos. 5,540,680; 5,895,385; 5,925,037; and 5,976,126, all entitled, "Endovascular Electrolytically Detachable Wire and Tip for the Formation of Thrombus in Arteries, Veins, Aneurysms, Vascular Malformations, and Arteriovenous Fistulas."

Still another coil deployment system incorporates a pusher member, having a stiff wavy-shaped wire end segment, coupled to an embolic coil and placed within the lumen of the catheter. The coil is advanced through the catheter until it reaches the predetermined site within the vessel, at which time the pusher member is retracted and the embolic coil is released. Such a system is disclosed in U.S. Pat. No. 6,203,547, entitled, "Vaso-occlusion Apparatus Having a Manipulable Mechanical Detachment Joint and a Method for Using the Apparatus."

Still another embolic device deployment system includes an elongated flexible pusher member slidably disposed within a lumen of a catheter. An embolic device is retained at the end of the pusher member with a detachment filament. When the embolic device is advanced to the predetermined site within the vessel, the detachment filament is withdrawn releasing the embolic device. Such a system is disclosed in U.S. patent application Ser. No. 11/145,350 filed on Jun. 3, 2005, entitled, "Embolic Device Deployment System with Filament Release."

SUMMARY OF THE INVENTION

The present invention is directed toward a vasooclusive embolic device deployment system for use in placing an embolic device at a predetermined site within a vessel including an elongated flexible catheter and an elongated pusher member slidably disposed within the lumen of the catheter. Disposed at the distal end of the pusher member is an embolic device having a headpiece with a cylindrical outer surface.

In accordance with an aspect of the present invention a retractable fiber, preferably formed of nitinol, includes a distal section, which is sufficiently stiff to maintain a preshaped configuration. This distal section is pre-shaped into a coiled configuration. When the fiber is pulled proximally the coiled configuration stretches to return to a generally straight configuration, to thereby release the embolic device at the predetermined treatment site within the vessel. The retractable fiber extends from a position proximal of the proximal end of the device through the lumen of the catheter and around the headpiece of the embolic device. The retractable fiber may fill the luminal space around the headpiece of the embolic device, such that the embolic device is frictionally held until a proximal force is applied to the fiber.

In accordance with another aspect of the present invention, the pusher member includes a lumen therethrough, and the embolic device is slidably disposed within the lumen at the distal end of the pusher member. The retractable fiber extends from a position proximal of the proximal end of the pusher member, through the lumen of the pusher member and around the outer surface of the headpiece of the embolic device. The fiber may fill the luminal space around the headpiece of the embolic device is held frictionally within the lumen at the distal end of the pusher member.

In accordance with yet another aspect of the present invention, a releasable clamp having a lumen extending therethrough is mounted on the proximal end of the pusher member. The detachment fiber extends through the lumen of the clamp, so that upon release of the clamp the retractable fiber may be pulled proximally to unwind it from around the headpiece of the embolic device at the predetermined site within the vessel.

These aspects of the invention and the advantages thereof will be more clearly understood from the following descriptions and drawings of a preferred embodiment of the present invention.

BRIEF DESCRIPTION OF THE DRAWINGS

FIG. 1 is an enlarged, partially sectional view of an embodiment of an embolic device deployment system in accordance with the present invention; and, FIGS. 2a, 2b, and 2c are enlarged, sectional views of the distal end of coil deployment system shown in FIG. 1, illustrating the sequential steps in the advancement of the embolic device, removal of a retractable fiber, and release of an embolic device at the predetermined treatment site within the vessel.

DESCRIPTION OF THE PREFERRED EMBODIMENT

Figure 2A:
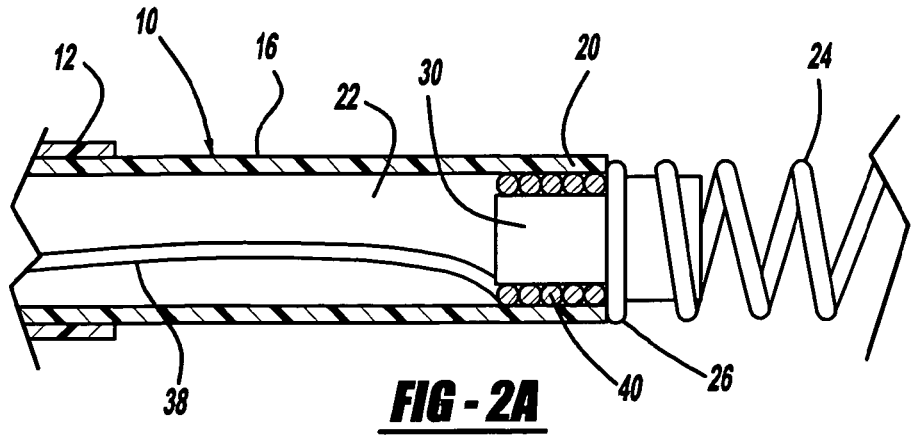

FIG. 1 generally illustrates one embodiment of a retractable detachment fiber arrangement of an embolic device deployment system 10 of the present invention including an elongated flexible catheter 12 having a lumen 14 therethrough. An elongated flexible pusher member 16, having a proximal end 18 a distal end 20 and a lumen therethrough 22, is slidably disposed within the lumen 14 of the catheter 12. Preferably, the pusher 16 is constructed from Nitinol, but alternatively may be constructed from any flexible, biocompatible material, such as stainless steel, nylon, PTFE, other flexible materials, polymers, or composites.

An embolic device 24 having a proximal end 26 and a distal end 28, preferably taking the form of a helically wound embolic coil, is disposed within the lumen 22 of the distal end 20 of the pusher member 16. Alternatively, the embolic device may take the form of embolic filaments, braids, expandable meshes, foams and stents. Coupled to the proximal end 26 of the embolic device 24, there is a headpiece 30, preferably, having a cylindrical outer surface. The headpiece 30 of the embolic device 24 extends distally into the embolic device, as well as, proximally from the embolic device 24 into the lumen 22 of the distal end 20 of the pusher member 16. Additionally, a releasable clamp 32, preferably taking the form of Tuohy Borst connector, having a proximal end 34 and a distal end 36, is mounted on the proximal end 18 of the pusher member 16.

An elongated retractable fiber 38 is constructed, preferably, from Nitinol but may also be constructed from platinum, nylon, PTFE, or other flexible metals, polymers, or composites. Extending from a position proximal of the proximal end 34 of the clamp 32, the elongated retractable fiber 38 extends through the clamp 32, which maintains tension on the fiber 38. The retractable fiber 38 then extends through the lumen 22 of the pusher member 16, from the proximal end 18 toward the distal end 20, and around the outer surface of the headpiece 30 of the embolic device 24, preferably in a coiled configuration 40.

In order to prevent the fiber 38 from prematurely disengaging from around the headpiece of the embolic device, the clamp 32 maintains tension on the fiber 38. To allow for application of a proximal force to the fiber 38, the clamp 32 is loosened, such that the fiber may be withdrawn from around the outer surface of the embolic device 24 and the embolic device may be released at the predetermined site in the vessel.

Figure 2B:
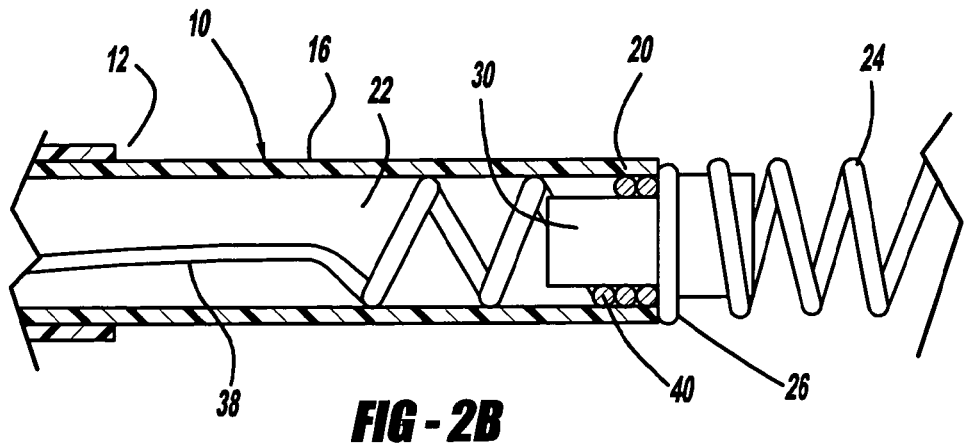
Figure 2C:
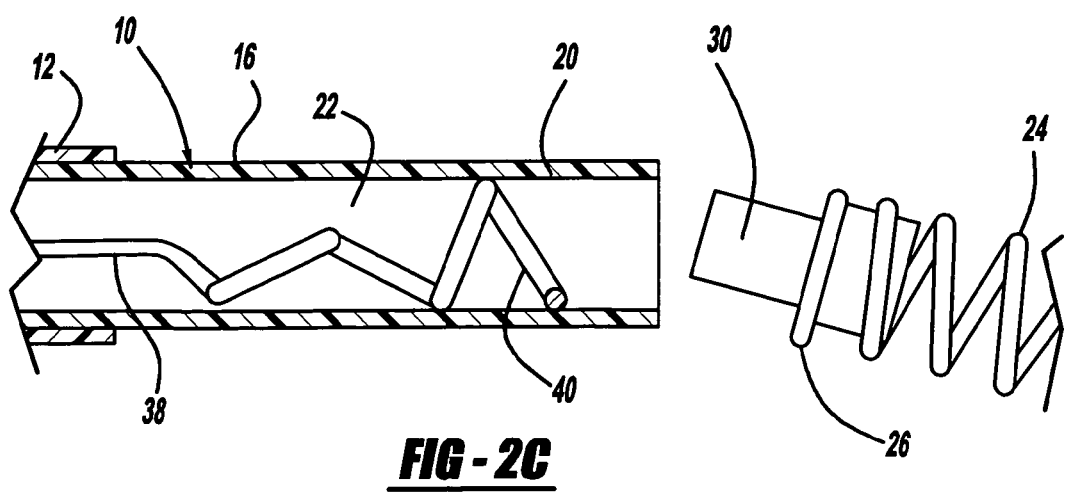

FIGS. 2a, 2b, and 2c generally illustrate the operation of the embolic device deployment system 10 and demonstrate the retractable fiber release mechanism of the present invention. More particularly, FIG. 2a illustrates the catheter 12 positioned at a predetermined location analogous to placement in a vessel and the pusher member 16 advanced, such that the embolic device 24 exits the distal end of the catheter. Also, illustrated in more detail is the path of the retractable fiber 38 around the headpiece 30 of the embolic device 24. The fiber extends through the lumen 22 of the pusher member 16 toward and subsequently around the headpiece 30 of the embolic device 24. Preferably, the detachment fiber 38 fills the luminal space around the outer surface of the headpiece 30 of the embolic device 24 in the coiled configuration 40 to frictionally hold the embolic device 24 within the distal end 20 of the lumen 22 of the pusher member 16. The coiled configuration 40 of the retractable fiber 38 may be preshaped, or, alternately, shaped around the headpiece as is necessitated by the material used to construct the fiber 38.

FIG. 2b illustrates the embolic device deployment system 10 of the present invention after proximal force has been applied to the retractable fiber 38, such that the retractable fiber 38 is partially disengaged from around the outer surface of the headpiece 30 of the embolic device 24. The coiled configuration 40 of the retractable fiber 38 need not straighten completely as proximal force is applied to the fiber 38. Such a coiled fiber configuration allows for a minimal proximal force to be used to disengage the coiled configuration 40 of the retractable fiber 38 from around the outer surface of the headpiece 30 of the embolic device 24.

FIG. 2c illustrates the coiled configuration 40 of the retractable fiber 38 further stretched, such that the detachment fiber 38 is completely disengaged from around the outer surface of the headpiece 30 of the embolic device 24. After the detachment fiber 38 is completely disengaged from around the outer surface of the headpiece 30, the embolic device 24 is no longer held frictionally within the lumen 22 of the distal end 20 of the pusher member 16, thereby releasing the embolic device 24 at the predetermined treatment site within the vessel.

One of the important advantages of the present invention is that the embolic device may be placed at a desired location within a vessel, or within an aneurysm, with the configuration of the device deployment system as shown in FIG. 2a. If it is determined that the embolic device is improperly positioned, the embolic device 24 may then be withdrawn from that location and placed at another location, or even removed from the body by first withdrawing the pusher member 16 and the embolic device totally back into the catheter. Once the embolic device has been entirely withdrawn back into the delivery catheter, the catheter may then be moved to a more desirable location and the embolic device may then be released at the new location.

As is apparent, there are numerous modifications of the preferred embodiment described above which will be readily apparent to one skilled in the art, such as many variations and modifications of the embolic device including numerous coil winding configurations, or alternately other types of implant devices. There are variations in the configuration of the distal section of the retractable fiber as well as variations in the material and flexibility of the proximal portion of the detachment fiber. Additionally, there could be variations the method in which tension is applied to the retractable fiber at the proximal end of the device. These modifications would be apparent to those having ordinary skill in the art to which this invention relates and are intended to be within the scope of the claims which follow.

That which is claimed is:

1. A vasooclusive embolic device deployment system for use in placing an embolic device at a predetermined site within a vessel comprising:
   an elongated flexible catheter having proximal and distal ends and a lumen extending therethrough;
   an elongated pusher member having proximal and distal ends and being slidably disposed within the lumen of the catheter;
   an embolic device having proximal and distal ends, and a headpiece having an outer surface disposed within the proximal end of the embolic device, and being disposed at the distal end of the pusher member; and,
   an elongated, retractable fiber extending from a position proximal of the proximal end of the pusher member, through the lumen of the catheter and around the outer surface of the headpiece of the embolic device such that the embolic device is held at the distal end of the pusher member until a proximal force is applied to the fiber and in so doing the retractable fiber stretches to disengage from around the headpiece of the embolic device to thereby release the embolic device at the predetermined site within the vessel; wherein the retractable fiber extends around the outer surface of the headpiece of the embolic device in a coiled configuration, an inner surface of the coiled configuration extends around the outer surface of the headpiece.

2. A vasooclusive embolic device deployment system as defined in claim 1, wherein said retractable fiber fills the luminal space around the headpiece of the embolic device, such that said embolic device is held frictionally within the lumen of the catheter.

3. A vasooclusive embolic device deployment system as defined in claim 1, wherein said pusher member has a lumen extending therethrough, said embolic device being slidably disposed within the lumen at the distal end of said pusher member and said retractable fiber extending from a position proximal of the proximal end of the pusher member through the lumen of the pusher member and around the headpiece of the embolic device such that the embolic device is frictionally held within the distal end of the pusher member.

4. A vasooclusive embolic device deployment system as defined in claim 1, wherein the outer surface of the headpiece of the embolic device is cylindrical.

5. A vasooclusive embolic device deployment system as defined in claim 1, wherein said retractable fiber is formed of nitinol.

6. A vasooclusive embolic device deployment system as defined in claim 1, wherein a releasable clamp having a lumen therethrough is mounted on the proximal end of the pusher member, said retractable fiber extending through the lumen of the clamp so that upon release of the clamp the detachment fiber may be pulled proximally to release the embolic device.

7. A vasooclusive embolic device deployment system for use in placing an embolic device at a predetermined site within a vessel comprising:
   an elongated flexible catheter having proximal and distal ends and a lumen extending therethrough;
   an elongated pusher member having proximal and distal ends and a lumen extending therethrough, and being slidably disposed within the lumen of the catheter;
   an embolic device having proximal and distal ends, and a headpiece disposed within the proximal end of the embolic device having an outer surface, and being slidably disposed within the lumen of the distal end of the pusher member; and,
   an elongated, retractable fiber extending from a position proximal of the proximal end of the pusher member, through the lumen of the pusher member, and filling the luminal space of said pusher member around the outer surface of the headpiece of the embolic device, such that the embolic device is frictionally held at the distal end of the pusher member until a proximal force is applied to the fiber and in so doing the retractable fiber stretches to disengage from around the headpiece of the embolic device to thereby release the embolic device at the predetermined site within the vessel; wherein the retractable fiber extends around the outer surface of the headpiece of the embolic device in a coiled configuration, an inner surface of the coiled configuration extends around the outer surface of the headpiece.

8. A vasoocclusive embolic device deployment system as defined in claim 7, wherein the outer surface of said headpiece of said embolic device is cylindrical.

9. A vasoocclusive embolic device deployment system as defined in claim 7, wherein said retractable fiber is formed of nitinol.

10. A vasoocclusive embolic device deployment system as defined in claim 7, wherein a releasable clamp having a lumen therethrough is mounted on the proximal end of the pusher member, said retractable fiber extending through the lumen of the clamp so that upon release of the clamp the detachment fiber may be pulled proximally to release the embolic device.

\* \* \* \* \*